United States Patent [19]
Pohl

[11] Patent Number: 5,421,205
[45] Date of Patent: Jun. 6, 1995

[54] APPARATUS FOR THE RAPID ULTIMATE MATERIAL STRENGTH TESTING OF TEST SAMPLES

[75] Inventor: Andreas Pohl, Gross-Umstadt, Germany

[73] Assignee: Carl Schenck AG, Darmstadt, Germany

[21] Appl. No.: 17,516

[22] Filed: Feb. 12, 1993

[30] Foreign Application Priority Data

Feb. 14, 1992 [EP] European Pat. Off. ............ 92102510

[51] Int. Cl.6 ............................................. G01N 3/08
[52] U.S. Cl. ........................................ 73/833; 73/859; 73/856
[58] Field of Search ................. 73/831, 833, 826, 828, 73/856, 857, 859, 860, 834, 835, 837

[56] References Cited

U.S. PATENT DOCUMENTS

| | | |
|---|---|---|
| 3,102,421 | 9/1963 | Cosner et al. |
| 3,388,592 | 6/1968 | Griffiths ............................ 73/833 |
| 3,407,651 | 10/1968 | Sophy |
| 4,426,875 | 1/1984 | Crosby, Jr. |

FOREIGN PATENT DOCUMENTS

| | | | |
|---|---|---|---|
| 0314829 | 5/1989 | European Pat. Off. | |
| 520078 | 12/1992 | European Pat. Off. | 73/826 |
| 2028030 | 6/1970 | Germany | 73/833 |
| 659932 | 4/1979 | U.S.S.R. | 73/831 |

OTHER PUBLICATIONS

Article Entitled: "A New Generation of High Speed Tensile Testing Machines" by Kussmaul et al., published in Measurement, vol. 9, No. 2, Apr.–Jun., 1991, pp. 73–80.
Derwent Abstract N89-106096 for EP (0314829).

Primary Examiner—Hezron E. Williams
Assistant Examiner—Nashmiya Ashraf
Attorney, Agent, or Firm—W. G. Fasse; W. F. Fasse

[57] ABSTRACT

The ultimate tensile strength of a test sample is tested in a high speed testing machine having a frame (2), a force measuring device (9A), and a load application mechanism (3, 4) for applying a loading stroke to the test sample after a loading piston has passed through a lead stroke to attain the required testing velocity. A force locking, frictionally effective clamping mechanism clamps the test sample for coupling to the machine frame (2) and/or to the load application mechanism (3) when the loading piston has reached the testing velocity.

13 Claims, 6 Drawing Sheets

APPARATUS FOR THE RAPID ULTIMATE MATERIAL STRENGTH TESTING OF TEST SAMPLES

FIELD OF THE INVENTION

The invention relates to an apparatus for the rapid ultimate material strength testing of test samples which are mounted in a machine frame to be exposed to a tensile load applied by a load application mechanism in an axial direction of the test sample. The load is applied after a load application member passes through a lead stroke to achieve the desired testing velocity.

BACKGROUND INFORMATION

In order to achieve a rapid ultimate strength testing of test samples exposed to tensile stress it is necessary to make sure that the loading velocity rises steeply at the beginning of the loading stroke to rapidly reach a predetermined loading velocity value. Conventional equipment for a rapid ultimate strength testing is provided with a lead stroke mechanism which establishes an acceleration or lead distance along which the load application device is accelerated to reach the predetermined velocity value. After passing through the lead distance, the stationary sample or body to be tested is coupled to the moving load application device and a loading force is thus transmitted to the sample or body to be tested.

In connection with conventional lead stroke devices problems have arisen at the instance of coupling the test sample to the load applicator after passing through the lead distance. These problems are due to the fact that the mass moved by the load applicator impacts on a stationary mass represented by the machine frame components connected to the test sample to be subjected to the ultimate tensile strength test. This impact is an elastic impact, whereby the load application device may be decoupled from the test sample, especially since a load application member must be accelerated for applying the test load. As a result, the respective masses are accelerated to different velocities. The decoupled component determines the required energy for breaking or rupturing the sample. This energy in turn depends on the decoupling speed and on the mass of the components involved.

European Patent Publication 0,314,829 (Beran et al.), published on May 10, 1989, relates to a machine for the rapid ultimate strength testing, wherein the above mentioned undesirable decoupling is substantially prevented in that the test sample to be exposed to an ultimate tensile load is provided with clamping jaws having outer wedge surfaces for cooperation with respective wedge surfaces arranged on the load application device or on a machine frame. Preparing the test samples with the wedge-shaped clamping jaws is rather expensive because the wedge surfaces on the test sample and the wedge surfaces on the counter-bearings require high precision machining work.

U.S. Pat. 4,426,875 (Crosby), granted on Jan. 24, 1984, discloses a strain measurement apparatus for measuring the elongation of a rope or cable under impact stress by attaching a light emitting diode to a free-falling weight which loads the rope upon impact. The test sample is connected with its upper end to the machine frame and the lower end of the test sample is provided with a further clamping device. During the testing the load application velocity required for the testing is achieved by a loading plate which is releasably arranged between the two ends of the test sample, and which is loaded with weights. The so loaded plate impacts onto the lower clamping device of the test sample after the plate and its weights pass through the lead distance.

U.S. Pat. No. 3,407,651 (Sophy), issued on Oct. 29, 1968, relates to a high speed tensile testing machine in which a test piece is subjected to a high tensile force exerted by a piston. The motion of the piston which is exposed to pressure, is initially prevented by a frangible member which is then rapidly fractured by the detonation of an explosive charge within the frangible member, whereby the pressurized piston is rapidly accelerated.

U.S. Pat. No. 3,102,421 (Cosner et al.) issued on Sep. 3, 1963, discloses a high speed tensile testing apparatus in which one end of the test sample is held by an anchor jaw and the other end is held by a clamping jaw on a freely movable specimen cross-head. A load sensor is installed between the specimen anchor jaw and a specimen bed rigidly attached to the main frame of the machine to provide a continuous stress sensing during a testing operation. When the hydraulic fluid flow rate corresponding to a desired test velocity is attained, a solenoid latch energizes and releases the driving crosshead, thereby permitting movement of an actuating assembly for applying the required tensile stress to the specimen or sample.

An article entitled: "A New Generation of High Speed Tensile Testing Machines" by Kussmaul et al., published in "Measurement", Volume 9, No. 2, April–June, 1991, discloses a high speed tensile testing machine for large scale specimens. Testing loads up to 12 Mega-Newtons (MN) may be applied to determine the influence of high loading rates on the stress and strain behavior of unwelded and welded components of ferritic and austenitic materials. The maximum tensile force is generated by a propellant charge with a piston velocity of 25 m/sec. after a lead stroke of 2 mm or a maximum velocity of 60 m/sec. after a lead stroke of 400 mm.

OBJECTS OF THE INVENTION

In view of the foregoing it is the aim of the invention to achieve the following objects singly or in combination:

to provide a high speed testing machine for testing the ultimate tensile strength of materials without the need of expensive surface matching machining operations, so as to maintain a simple and cost efficient construction of the clamping mechanisms, while still avoiding the above described decoupling;

to provide a coupling which causes the test sample to take on the velocity or speed of the load applying mechanism without any decoupling and thus instantaneously;

to assure an instantaneous, yet safe and certain force locking friction coupling between the test sample and the load application mechanism; and to assure an automatic operation of the pretensioning or biasing elements after the load application mechanism passes through a lead stroke.

SUMMARY OF THE INVENTION

According to the invention the following features are provided in combination in an apparatus for the rapid ultimate tensile strength testing of a test sample. A machine frame carries a load application mechanism performing a loading stroke to be applied to a test sample held in the machine frame, whereby a force measuring device, such as a load cell, is arranged for measuring the applied force. Coupling devices are provided for connecting the test sample either to the load application mechanism and/or to the machine frame after a load applying member has passed through a lead stroke. The coupling devices are so constructed that the coupling of the test sample takes place through force locking means by frictional force transmission without any decoupling.

According to the invention, after the load application member has passed through the lead stroke, the sample or specimen is coupled by force locking frictional devices to the machine frame and/or to the load application mechanism so that the sample is directly exposed to the desired or required breaking or rupture velocity as the coupling operation is completed instantaneously.

According to a preferred embodiment of the invention, the force locking frictional devices comprise biasing elements which are activated by respective activating members after a load applicator of the load application mechanism has passed through the lead stroke, thereby causing a force locking frictional coupling of the probe. This construction assures an instantaneous and certain coupling. In a preferred embodiment the above mentioned biasing elements are constructed as bolts which are arranged in a clamping block and which are biased in a direction toward the sample by spring cages or sleeves and nuts. Because such bolts, spring sleeves, and nuts as such are conventional shelf items, this construction is especially cost efficient.

An automatic operation or activation of the biasing elements after the load applicator or stroke member has passed through the lead stroke, is achieved by intermediate wedges releasably arranged in the clamping block. These wedges are released from the clamping block by stops arranged in the machine frame, preferably adjustably.

According to another preferred embodiment according to the invention a guide element comprises two blocks displaceably arranged on the machine frame for movement in a crosswise direction relative to the load application direction so that samples of different configurations can be tested in the same machine without substantial retooling. These blocks guide loading strap bars.

BRIEF DESCRIPTION OF THE DRAWINGS

In order that the invention may be clearly understood, it will now be described, by way of example, with reference to the accompanying drawings, wherein.

DESCRIPTION OF PREFERRED EXAMPLE EMBODIMENTS AND OF THE BEST MODE OF THE INVENTION

Figure 1:
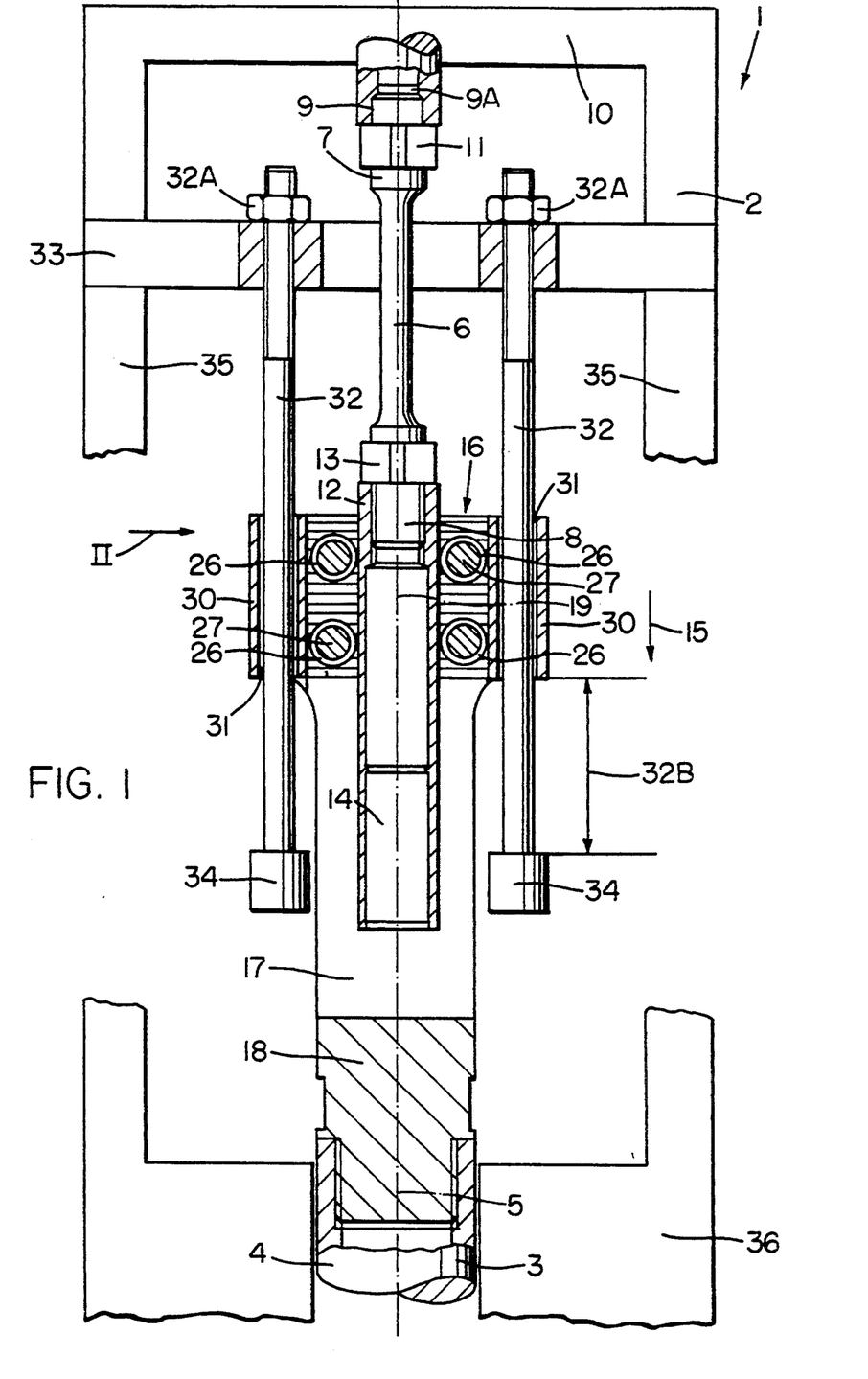
FIG. 1 is a sectional view along the section plane I—I in FIG. 2 of an apparatus according to the invention, with portions of the machine frame broken away.
Figure 2:
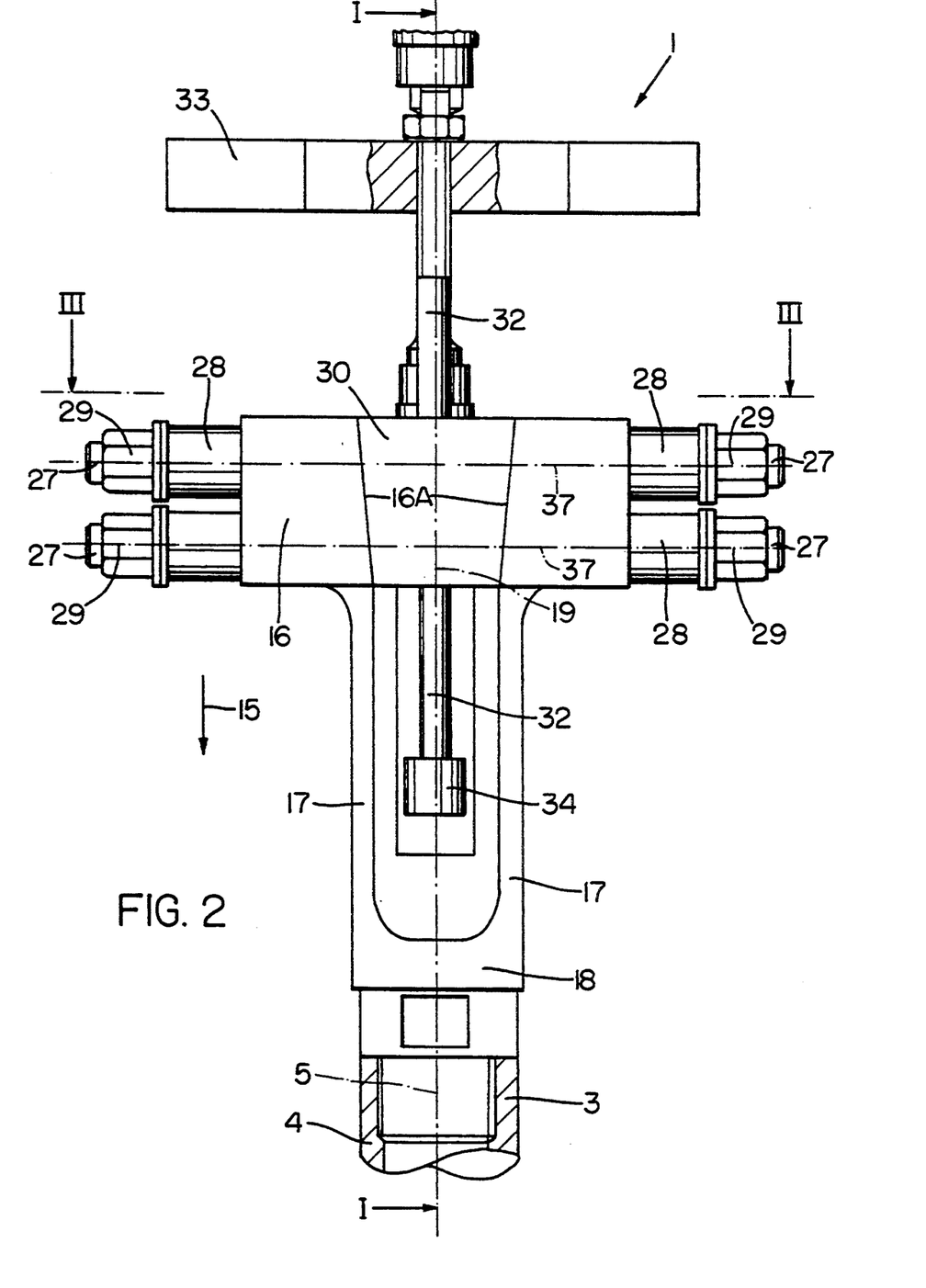
FIG. 2 is a side elevational view, partly in section, in the direction of the arrow II in FIG. 1.
Figure 3:
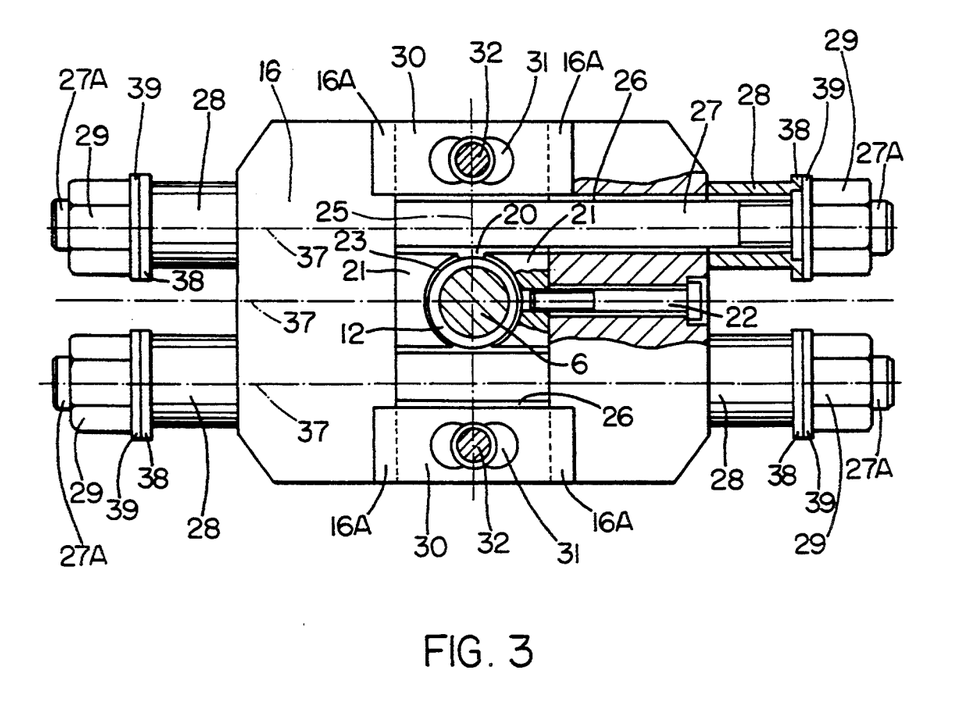
FIG. 3 is a sectional view along section plane III—III in FIG. 2.

FIGS. 1, 2 and 3 illustrate a high speed testing apparatus 1 for ultimate tensile strength testing of material samples. The apparatus comprises a machine frame 2 having mounted therein a load application mechanism 3 which includes, for example, a hydraulic cylinder and piston device 4 forming a load applying stroke member. The load application takes place centrally along the axis 5 which coincides with the central longitudinal axis 19 of the apparatus. The test sample 6 shown in FIG. 1 is a rod having a circular cross-section and a threaded upper head 7 as well as a threaded lower end 8. The threaded upper head 7 is threaded into a threaded bushing 9 holding a load cell 9A and connected to the cross-piece 10 of the machine frame 2. The cross-piece 10 interconnects the uprights 35 of the machine frame 2. The bushing 9 is rigidly connected to the cross-piece 10, however, the load cell 9A is operatively inserted between the cross-piece 10 and the bushing 9. A counter-nut 11 is mounted on the threaded upper head 7 of the sample 6 in order to rigidly secure the sample 6 to the bushing 9 with the help of the counternut 11 which bears against the mounting bushing 9.

The test sample 6 to be tested in the embodiment shown in FIGS. 1, 2, and 3, is relatively short, so that the length of the sample itself is too short for the above mentioned lead distance or acceleration distance of the stroke piston 4. Therefore, an adapter piece 12 is screwed with its inner threaded upper end onto the threaded lower end 8 of the sample 6. A counternut 13 bearing against the facing end of the adapter 12 rigidly secures the adapter 12 to the sample 6. The adapter 12 is formed as a sleeve, for example. A stabilizing bolt 14 is inserted coaxially into the adapter sleeve 12. The lower end of the adapter sleeve 12 reinforced by the stabilizing bolt 14 is connectable to a clamping block 16 as soon as the stroke piston 4 has moved through the lead distance in the direction of the arrow 15. The clamping block 16 is rigidly connected to the stroke piston 4 by two force transfer strap bars 17 interconnected by a cylindrical strap body 18 which in turn is secured to the free end of the stroke piston 4 forming the load applicator or stroke member.

As shown in FIG. 3, the clamping block 16 comprises a substantially quadrangular configuration with a central through-going opening 20 concentric with its central axis 19, and with the load application axis 5 as shown in FIG. 1. The axis 5 and the axis 19 extend perpendicularly to the drawing sheet in FIG. 3. The through-going opening 20 also has a rectangular cross-section. Two clamping jaws 21 reach into the through-going opening 20 from opposite wall surfaces of the clamping block 16 facing into the opening 20. Each clamping jaw 21 is held in position by a respective screw 22 securing the clamping jaws 21 to the clamping block 16. Each clamping jaw 21 is provided with ridges and grooves 23 for securely clamping the adapter sleeve 12. The clamping jaws 21 are so constructed that the respective grooves and ridges 23 form approximately a semicircle for engaging the adapter sleeve 12. The resulting circle has a diameter adapted to the outer diameter of the sleeve 12, whereby in the open position of the clamping jaws 21 there remains a gap of about 0.1 mm between the sleeve 12 and the ridges 23 of the clamping jaws 21.

As shown in the view of FIG. 3, the clamping block 16 is constructed symmetrically relative to a view horizontal central axis 24 and a view vertical central axis 25 that cross each other at right angles, whereby both axes 24 and 25 cross the third central axis 19 at right angles in the center of FIG. 3.

Referring again to FIG. 1, a total of four horizontal through-bores 26 are symmetrically arranged in the clamping block 16. These through-bores 26 form an upper pair of bores and a lower pair of bores The upper pair of bores is positioned above the central plane of the block defined by the axis 24 and 25 while the lower pair of bores is positioned below this central plane in the block 16. The through-bores 26 are uniformly spaced from each other and relative to the central axis. The upper pair of through-bores is vertically spaced from the lower pair of through-bores and symmetrically relative to the central plane defined by the axis 24 and 25. A bolt 27 passes through each through-bore 26. Each bolt 27 has two threaded ends 27A which project sufficiently outside the body of the block 16 to hold a spring cage 28 having a flange 38 bearing against a washer or flange 39 of a clamping nut 29 as best seen in FIG. 3. The opposite end of each spring cage 28 bears against the clamping block 16. By tightening or loosening the nuts 29 the biasing or pretensioning of the bolts 27 is adjustable.

As shown in FIGS. 2 and 3 taken in conjunction, the clamping block 16 comprises two wedge-shaped recesses with slanting wedge walls 16A. These wedge walls 16A taper downwardly and axially inwardly so that each wedge-shaped recess is wider at the top of the block 16 than at the bottom of the block 16 as best seen in FIG. 2. Each wedge-shaped recess holds a downwardly tapering wedge 30 engaging the walls 16A. Each wedge 30 has a central through-going hole 31 having an elongated cross-section as best seen in FIG. 3. A threaded bolt 32 with a downwardly facing stop head 34 passes through each through-hole 31 in each wedge 30. The upper end of each bolt 32 is threaded and held by a nut 32A against a cross-head 33 interconnecting the uprights 35 of the machine frame 2, whereby the lead stroke or lead distance 32B is adjustable as best seen in FIG. 1. The stop heads 34 shown in FIG. 1 have a diameter that is larger than the width of the through-holes 31.

The operation of the first embodiment will now be described with reference to FIGS. 1, 2, and 3. Prior to beginning a test, the upper head 7 of the sample 6 is rigidly secured to the machine frame 2 while the lower end of the sample 6 having attached thereto the adapter sleeve 12, passes with said sleeve through the opening 20 of the clamping block 16 toward the load application mechanism 3. Now the load application stroke piston 4 carrying the clamping block 16 through the two straps 17 is first moved upwardly opposite to the load application direction 15 toward the sample 6. When the block 16 has reached its desired lead stroke position the piston 4 is accelerated downwardly in the direction of the arrow 15 to reach the required or predetermined testing velocity. At the moment when the piston with the block 16 has passed through the lead stroke 32B, the wedges 30 hit the stop heads 34 of the bolts 32, whereby the wedges 30 are forced instantaneously upwardly and out of the recesses formed by the slanting walls 16A. Due to the biasing by the bolts 27 inwardly in the direction of the axis 24, the sleeve 12 is instantaneously gripped by the clamping jaws 21 in a frictional, force transmitting manner, whereby the stabilizing insert bolt 14 in the lower end of the adapter sleeve 12 prevents any buckling or crushing of the sleeve 12.

The sample 6 is now coupled to the moving mass of the stroke piston or member 4 through the sleeve 12, the clamping jaws 21, and the clamping block 16, whereby the desired breaking or rupture velocity is applied to the sample 6. The lead stroke 32B is determined by the length of the bolts 32 and thus the position of the stop heads 34 at the lower ends of the bolts 32. The stop head 34 may be threaded onto the lower ends of the bolts 32, thereby providing one possibility of adjusting the lead stroke 32B. Additionally, or in the alternative, the lead stroke 32B may be adjusted by the nuts 32A as mentioned above.

Due to the provision of the adapter sleeve 12 for short samples 6, the introduction of the testing load into the sample 6 is slightly delayed following the passage of the piston 4 through the lead stroke 32B. However, such a slight delay can be easily avoided by connecting the upper head 7 of the sample 6 to the frame 2 through an adapter sleeve and permitting the action of the clamping jaws 21 to be directly effective on the lower end of the test sample. Thus, the testing load is directly applied to the test sample 6 after the piston has passed through the lead stroke 32B, whereby the above mentioned short time delay is altogether avoided.

Figure 4:
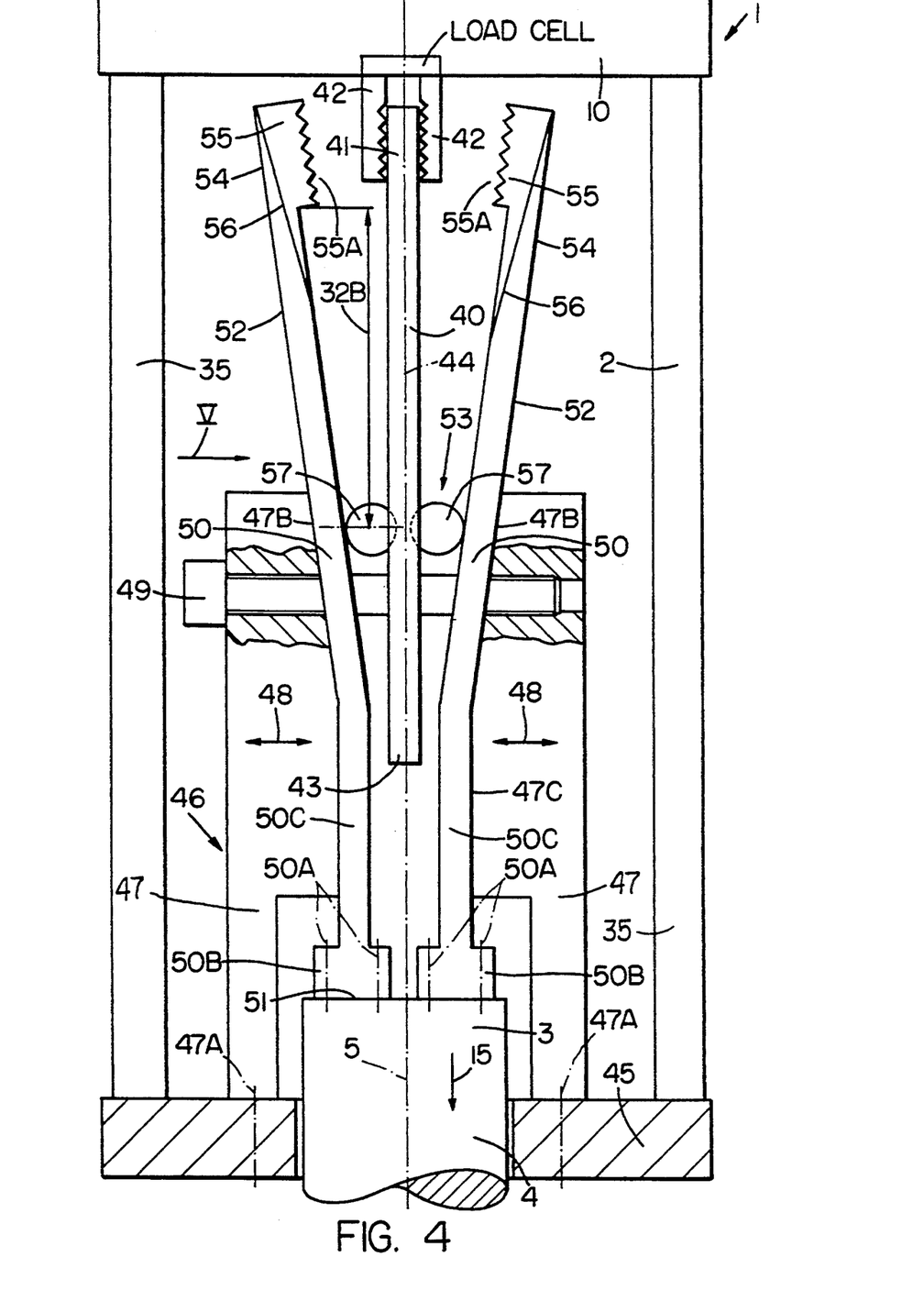
FIG. 4 is an elevational view, partially in section, of a second embodiment of an apparatus according to the invention with test clamping jaws shown in an open state.
Figure 5:
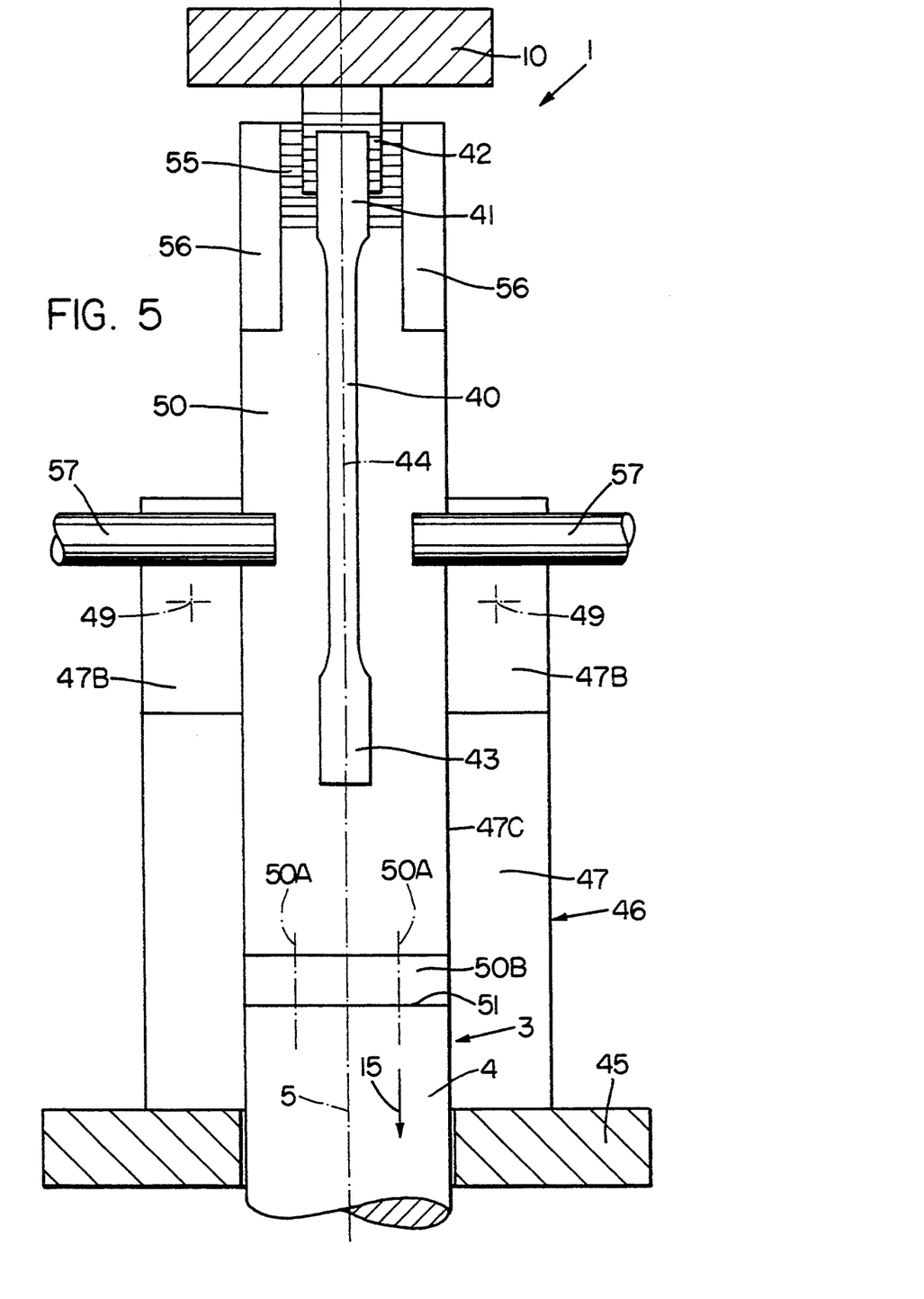
FIG. 5 is a view in the direction of the arrow V in FIG. 4, and partially in section.

FIGS. 4 and 5 disclose a further embodiment of a high speed ultimate tensile strength testing apparatus according to the invention. Those components which are the same in FIGS. 4 and 5 as in FIGS. 1, 2, and 3 are provided with the same reference numbers.

The example embodiment of FIGS. 4 and 5 is constructed for testing flat samples 40 having an upper end 41 rigidly clamped to the machine frame by two clamping jaws 42. The lower end 43 of the flat sample 40 extends centrally along the central axis 44 toward the load application mechanism 3. The longitudinal central axis 44 of the sample 40 coincides with the load application axis 5 of the mechanism 3. The machine frame 2 of the apparatus 1 comprises a lower cross-piece 45 interconnected with the upper cross-piece 10 by the uprights 35. A guide mechanism 46 comprising two guide members 47 is operatively secured to the lower cross-piece 45 as symbolically indicated at 47A. However, the connection 47A permits an adjustment or displacement of the guide elements 47 horizontally back and forth as indicated by the respective double arrows 48 to accommodate test samples 40 of different sizes.

The upper ends of each of the guide members 47 of the guide mechanism 46 are provided with slanting surfaces 47B. These slanting surfaces 47B form ramps that slant downwardly and axially inwardly as best seen in FIG. 4. Thus, these ramps 47B form a conical or wedge-shaped recess 53 that opens upwardly and narrows downwardly. Each guide member 47 has a central section 47C formed as an approximately semi-circular trough through which the lower ends 50C of sample gripping strap bars 50 extend. These lower ends 50C of the bars 50 have mounting feet 50B secured to the axially facing end surface 51 of the piston 4 by screws 50A. The gripping strap bars 50 are of sufficient flexibility for causing the upper clamping jaws 55 to move toward each other for gripping the lower end 43 of the sample 40, as will be described in more detail below. In FIG. 4 the jaws 55 are still open. The guide members 47 are interconnected by screws 49 as best seen in FIG. 4. The screws 49 only shown symbolically in FIG. 5, pass through the slanting ramps 47B forming the recess 53.

The sample gripping strap bars 50 extend from the facing end 51 of the piston rod 4 upwardly toward the upper cross-piece 10 into a zone next to the clamping jaws 42 which hold the upper end 41 of the test sample 40. This position of the gripping strap elements 50 is taken up at the beginning of a test sequence.

Both FIGS. 4 and 5 show this position. The mounting of the gripping strap elements 50 to the piston 4 is such that the test sample 40 is centered between the two gripping strap elements 50.

The sample gripping strap bars 50 are so constructed that at least a section along the length of each strap bar 50 having a surface 52 facing away from the sample 40 rests in a sliding manner against the slanting surfaces 47B forming the conical recess 53 between the guide members 47. Each upper end 54 of the strap bars 50 is provided centrally with one of the above mentioned clamping jaws 55 having teeth 55A. Each clamping jaw 55 is positioned centrally between two guide ramps 56. These ramps taper downwardly and axially inwardly while opening in the upward direction.

Figure 6:
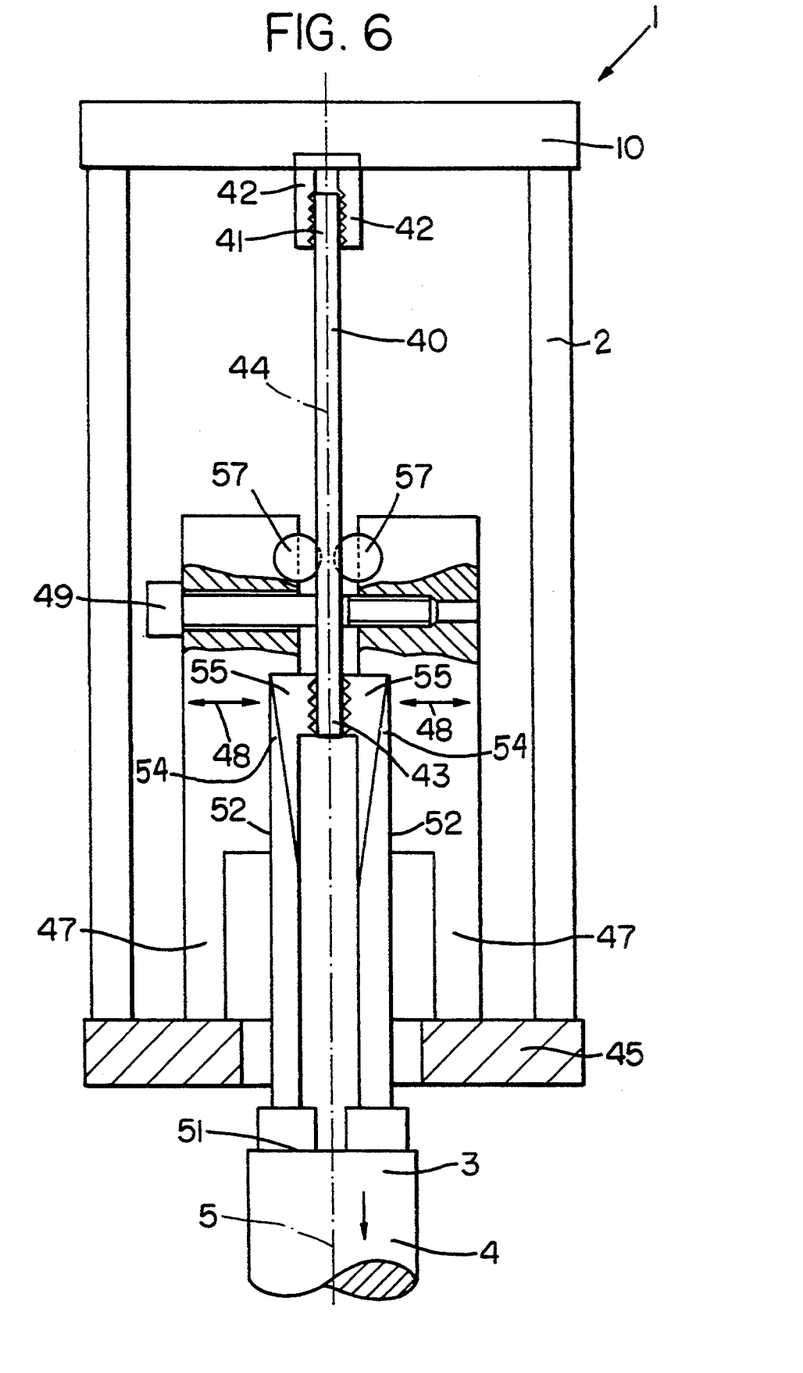
FIG. 6 is a view as in FIG. 4, but with the test clamping jaws shown in the closed state.

Prior to the beginning of a testing operation, the stroke piston 4 and the gripping strap bars 50 secured thereto, are positioned as shown in FIGS. 4 and 5. A test sample 40 is held by the claws 42 with its free lower end 43 centrally positioned as shown. The stroke piston 4 is then accelerated downwardly in the direction of the arrow 15, whereby the strap bars 50 slide down through the lead stroke or distance 32B shown in FIG. 4 until the teeth 55A of the claws 55 rigidly clamp the lower free end 43 of the sample 40 as shown in FIG. 6. This force transmitting friction clamping is instantaneously achieved as the surfaces 52 slide down on the inclined ramps 47B of the guide elements 47. As soon as the upper ramps 56 engage the guide rollers 57, the clamping begins. During the lead stroke 32B, the rollers 57 also guide the strap bars 50 by engaging the marginal areas below the ramps 56 of the strap bars 50. The strap bars 50 with their clamping heads 55 thus function as powerful tweezers, whereby the sample 40 is torn apart with the energy which the piston 4 transfers onto the test sample at the required testing velocity.

Although the invention has been described with reference to specific example embodiments, it will be appreciated that it is intended to cover all modifications and equivalents within the scope of the appended claims.

What I claim is:

1. An apparatus for the high velocity ultimate tensile strength testing of a test sample, comprising a machine frame (2), load application means (3) mounted in said machine frame and including a stroke member (4) for applying, a testing load to said test sample (6, 40), means for connecting said test sample to said machine frame and to said load application means (3), a load cell positioned for measuring said testing load applied to said test sample, said connecting means comprising a frictionally effective force transmitting advice for applying said testing load to said test sample in response to said stroke member having passed through a lead stroke and having achieved a required testing stroke velocity, wherein said frictionally effective force transmitting device comprises a biasing element effective on said force transmitting device and activating means for controlledly counteracting said biasing element in response to said stroke member passing through said lead stroke, whereby said force transmitting device causes a force transmitting frictional coupling of said test sample to one member selected from the group consisting of said stroke member and said machine frame.

2. The apparatus of claim 1, wherein said force transmitting device of said connecting means comprises a clamping mechanism for positively friction coupling a first end of said test sample to said stroke member of said load application means, said connecting means further comprising means for rigidly securing a second end of said test sample to said machine frame.

3. The apparatus of claim 2, wherein said second test sample end is an upper test sample end rigidly connected to said machine frame by said securing means, and wherein said first test sample end is a lower test sample end coupled to said stroke member of said load application means (3) when said stroke member has just passed through said lead stroke and has achieved said stroke velocity.

4. The apparatus of claim 1, wherein said biasing elements comprises bolts (27) under tension in a biasing direction toward said test sample (6).

5. The apparatus of claim 4, further comprising clamping block elements forming a clamping block (16), means connecting said clamping block to said load application means, said bolts passing through said clamping block, and nuts on said bolts for biasing said bolts to force said clamping block elements toward each other.

6. The apparatus of claim 5, wherein said activating means comprise intermediate wedges (30) removably inserted in said clamping block (16) between said clamping block elements, said bolts (27) having threaded ends projecting from said clamping block, said nuts being received on said threaded bolt ends, and spring means on said projecting bolt ends between said nuts and said clamping block for adjusting a biasing force.

7. The apparatus of claim 6, wherein said spring means comprise spring cages (28) or spring sleeves.

8. The apparatus of claim 6, further comprising stop means (34) secured to said machine frame (2) for removing said intermediate wedges (30) from said clamping block (16) in a direction substantially perpendicular to said biasing direction when said stroke member (4) of said load application means (3) has passed through said lead stroke.

9. The apparatus of claim 1, wherein said frictionally effective force transmitting device comprises strap bars (50) with clamping heads (55) connected to said stroke member of said load application means (3), and a guide element (46) for guiding movement of said strap bars, wherein said strap bars form said biasing element and said guide element forms said activating means.

10. The apparatus of claim 9, wherein said guide element (46) comprises two blocks (47) mounted for displacement on the machine frame (2), said blocks (47) having conically configured guide surfaces (47B) facing toward each other and forming a guide passage (53) for said strap bars (50).

11. The apparatus of claim 10, further comprising guide rollers (57) mounted rotationally in said machine frame, and wherein said strap bars (50) are guided along said surfaces (47B) of said blocks (47) and by said guide rollers (57).

12. An apparatus for the high velocity testing of the tensile strength of a test sample in a testing direction, comprising a machine frame, a stroke member arranged to be driven relative to said machine frame in the testing direction through a lead stroke and a testing stroke sequentially following said lead stroke, a clamping member connected to said machine frame or to said stroke member, wherein said clamping jaws are arranged substantially symmetrically about an axis of the test sample extending in the testing direction, and wherein said clamping jaws are adapted to move in a direction substantially perpendicular to the testing direction so as to clamp the test sample when said lead stroke has been completed and said testing stroke is to begin.

13. The apparatus of claim 12, further comprising a clamp urging member arranged on said clamping member and urging said clamping jaws toward one another in the direction substantially perpendicular to the testing direction, and a clamp restraining member arranged to engage said clamping member and restrain said clamping jaws from moving toward one another during said lead stroke and to disengage from said clamping member and allow said clamping jaws to move toward one another after said lead stroke when said testing stroke is to begin.

* * * * *

UNITED STATES PATENT AND TRADEMARK OFFICE
CERTIFICATE OF CORRECTION

PATENT NO. : 5,421,205
DATED : June 6, 1995
INVENTOR(S) : Pohl

It is certified that error appears in the above-identified patent and that said Letters Patent is hereby corrected as shown below:

Column 2, line 40, replace "2 mm" by --20 mm--.

Column 5, line 10, after "bores" (second occurrence) insert --.--.

Claim 12, column 9, line 1, after "member," insert --and at least two clamping jaws provided on said clamping member,--.

Signed and Sealed this

Twenty-ninth Day of August, 1995

Attest:

BRUCE LEHMAN

Attesting Officer    Commissioner of Patents and Trademarks